(12) United States Patent
Tilly et al.

(10) Patent No.: US 7,195,775 B1
(45) Date of Patent: Mar. 27, 2007

(54) PROTECTION OF THE FEMALE REPRODUCTIVE SYSTEM FROM NATURAL AND ARTIFICIAL INSULTS

(75) Inventors: Jonathan L. Tilly, Windham, NH (US); Richard N. Kolesnick, New York, NY (US)

(73) Assignee: The General Hospital Corporation, Boston, MA (US)

( * ) Notice: Subject to any disclaimer, the term of this patent is extended or adjusted under 35 U.S.C. 154(b) by 911 days.

(21) Appl. No.: 09/503,852

(22) Filed: Feb. 15, 2000

(51) Int. Cl.
*A61F 6/00* (2006.01)
*A01N 57/00* (2006.01)

(52) U.S. Cl. ..................... 424/430; 514/114
(58) Field of Classification Search ............... 514/114; 424/422, 423, 430, 434, 435
See application file for complete search history.

(56) References Cited

U.S. PATENT DOCUMENTS 5,712,262 A * 1/1998 Spiegel ..................... 514/114
5,877,167 A * 3/1999 Igarashi et al. ............ 514/114

OTHER PUBLICATIONS

Morita, Y., et al., "Oocyte Apoptosis: Like Sand Through An Hourglass", Dev. Biol., vol. 213, No. 1, pp. 1-17 (1999).
Morita, Y., et al., "Requirement For Phosphatidylinositol-3"-Kinase In Cytokine-Mediated Germ Cell Survival During Fetal Oogenesis In The Mouse", Endocrinology, vol. 140, No. 2, pp. 941-949 (1999).
Morita, Y., et al., "Targeted Expression Of Bcl-2 In Mouse Oocytes Inhibits Ovarian Follicle Atresia And Prevents Spontaneous And Chemotherapy-Induced Oocyte Apoptosis In Vitro", Mol. Endocrinology, vol. 13, No. 6, pp. 841-850 (1999).
Hla, T., et al., "Shingosine-1-Phosphate: Extracellular Mediator Or Intracellular Second Messenger?", Biochem. Pharmacol, vol. 58, No. 2, pp. 201-207 (1999).
Perez, G., et al., "Fragmentation And Death (A.K.A. Apoptosis) Of Ovulated Ooctyes", Mol. Human Reprod., vol. 5, No. 5, pp. 414-420 (1999).
Reynolds, T.., "Cell Death Genes May Hold Clues To Preserving Fertility After Chemotherapy", J. Nat'l Cancer Inst., vol. 91, No. 8, pp. 664-666 (1999).
Perez, G., et al., "Prolongation of Ovarian Lifespan Into Advanced Chronological Age By Bax-Deficiency", Nature Genet., vol. 21, No. 2, pp. 200-203 (1999).
Spiegel, S., Sphingosine 1-Phosphate: A Prototype Of A New Class Of Second Messengers, J. Leukocyte Biol., vol. 65, No. 3, pp. 341-344 (1999).
Spiegel, S., et al., "Sphingosine-1-Phosphate In Cell Growth And Cell Death", Ann. N.Y. Acad. Sci., vol. 845, pp. 11-18 (1998).
Bergeron, L., et al., "Defects In Regulation Of Apoptosis In Caspase-2-Deficient Mice", Genes. Dev., vol. 12, pp. 1304-1314 (1998).
Goetzl, E., et al., "Diversity Of Cellular Receptors And Functions For The Lysophospholipid Growth Factors Lysophosphatidic Acid And Sphingosine 1-Phosphate", FASEB J., vol. 12, No. 15, pp. 1589-1598 (1998).

Perez, G., et al., "Apoptosis-Associated Signaling Pathways Are Required For Chemotherapy-Mediated Female Germ Cell Destruction", vol. 3, No. 11, pp. 1228-1232 (1997).
Cuvillier, O., et al., "Suppression of Ceramide-Mediated Programmed Cell Death By Sphingosine-1-Phosphate", Nature, vol. 381, No. 6585, pp. 800-803 (1996).
K., Horinouchi, et al., "Acid Sphingomyelinase Decicient Mice: A Model of Types A and B Niemann-Pick Disease", Nat. Genet., vol. 10, No. 3, pp. 288-293 (1995).
Edsall, L. C., et al., "Involvement Of Sphingosine 1-Phosphate In Nerve Growth Factor-Mediated Neuronal Survival And Differentiation", J. Neurosci., vol. 17, pp. 6952-6960 (1977).
Abstract, Tilly et al., "Shingolipid signaling in gonadal development and function" abstract No. 623565, Chem. Abstracts vol. 131, No. 349341 (1999).
Abstract, Morita et al., "Oocyte apoptosies is suppressed by disruption of the acid shingomyelinase gene or by sphingosine-1-phosphate therapy", abstract No. 736446, Chem. Abstracts, vol. 134, No. 25322 (2000).
Abstract, Casper et al., "Protecting the Female Germ Line from Cancer Therapy", Elsevier Science Publishers, Amsterdam. No. 2000375706 (2000).
Gong et al., "The tyrosine kinase c-Abl regulates p73 in apoptotic response to cisplatin-induced DNA damage", Nature, (1999) 399:806-809.
Springer et al., "Involvement of Apoptosis in 4-Vinylcyclohexene Diepoxide-Induced Ovotoxicity in Rats", Toxicol. Appl. Pharmacol., (1996) 139:394-401.
Perez and Tilly, "Cumulus cells are required for the increased apoptotic potential in oocytes of aged mice", Human Reproduction (1997) 12:2781-2783.
Perez et al., "Prolongation of ovarian lifespan into advanced chronological age by *Bax*-deficiency", Nature Genetics, (1999) 21:200-203.
Kugu et al., "Analysis of apoptosis and expression of *bcl*-2 gene family members in th ehuman and baboon ovary", Cell Death and Differentiation, (1998) 5:67-76.
Flaws et al., "Vasoactive intestinal peptide-mediated suppression of apoptosis in the Ovary: Potential Mechanisms of Action and Evidence of a conserved antiatreogenic role through evolution", Endocrinol. (1995) 136:4351-4359.

(Continued)

Primary Examiner—Michael G. Hartley
(74) Attorney, Agent, or Firm—Edwards Angell Palmer & Dodge LLP

(57) ABSTRACT

Described are methods for protecting the female reproductive system against natural and artificial insults by administering to women a composition comprising an agent that antagonizes one or more acid sphingomyelinase (ASMase) gene products. Specifically, methods disclosed herein serve to protect women's germline from damage resulting from cancer therapy regimens including chemotherapy or radiotherapy. In one aspect, the method preserves, enhances, or revives ovarian function in women, by administering to women a composition containing sphingosine-1-phosphate, or an analog thereof. Also disclosed are methods to prevent or ameliorate menopausal syndromes and to improve in vitro fertilization techniques.

17 Claims, 4 Drawing Sheets-

OTHER PUBLICATIONS

Figure 1:
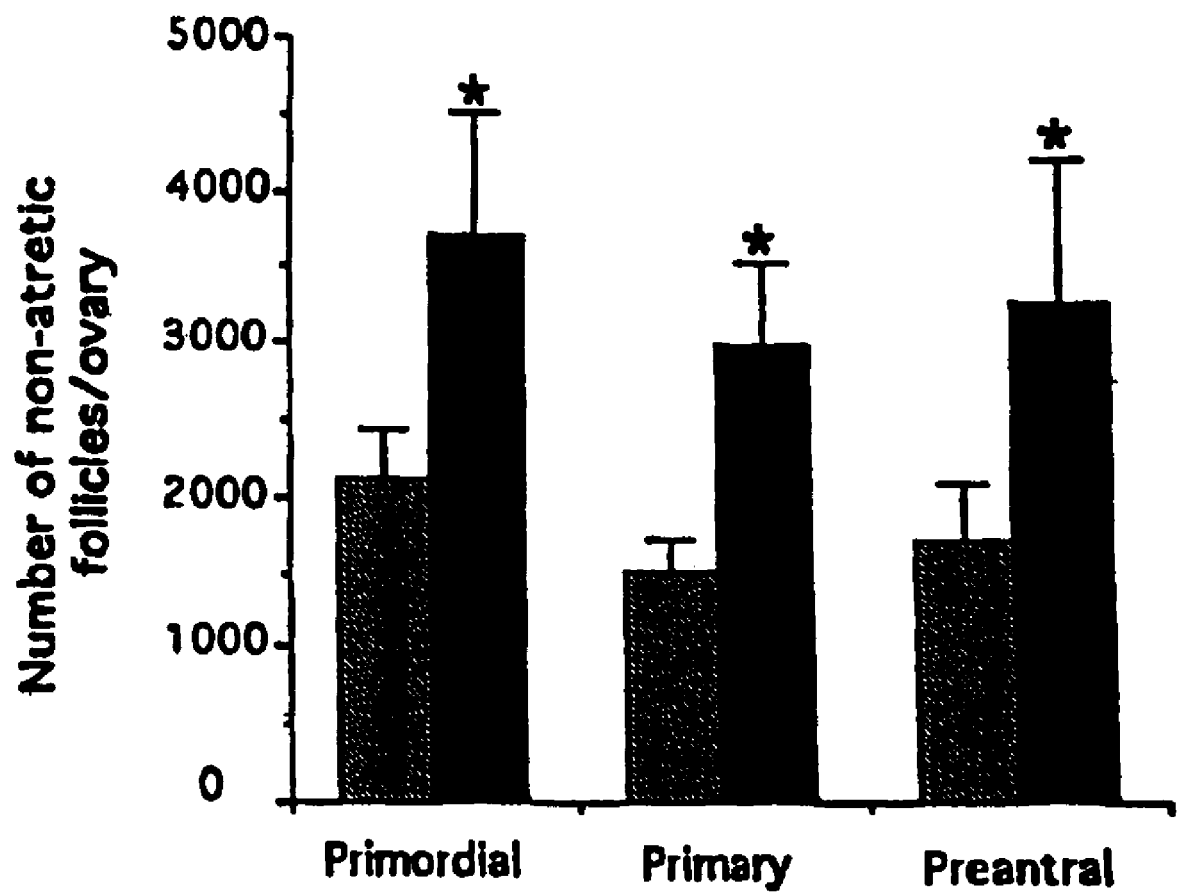

Tilly et al., "Epidermal growth factor and basic fibroblast growth factor suppress the spontaneous onset of apoptosis in cultured rat ovarian granulosa cells and follicles by a tyrosine kinase-dependent mechanism", *Mol. Endocrinol.*, (1992) 6:1942-1950.

Johnson et al., "Susceptibility of Avian Ovarian Granulosa cells to apoptosis is dependent upon stage of follicle development and is related to endogenous lvels of *bcl*-xlong gene expression", *Endocrinol.* (1996) 137:2059-2066.

Greco RM. et al., "Differences in cell division and thymidine incorporation with rat and primate fibroblasts in collagen lattices", *Tissue Cell.*, (1992) 24:6 843-851.

* cited by examiner

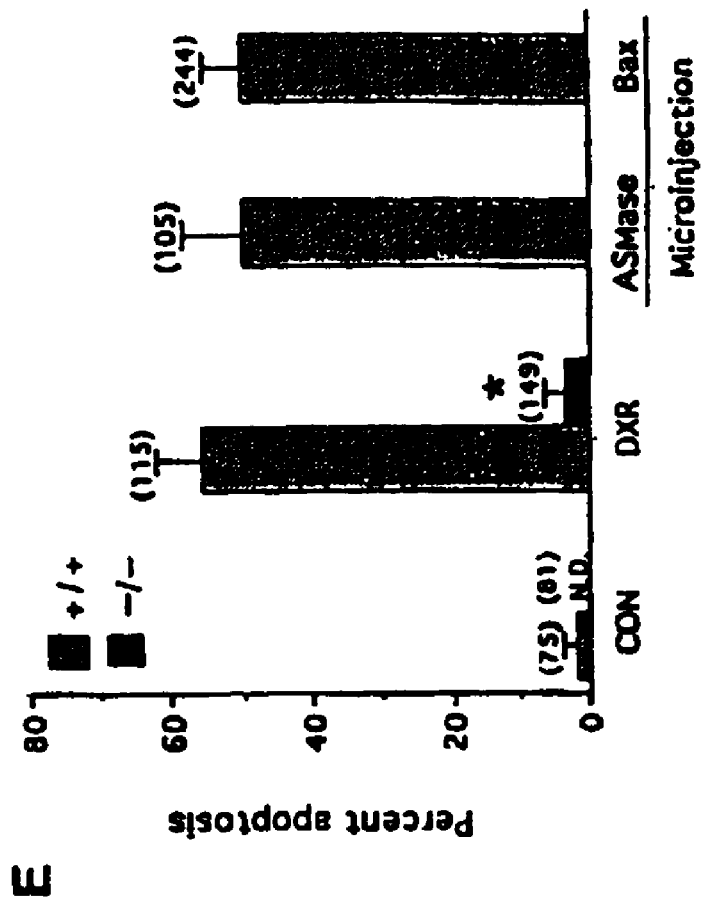
Figure 3a
Figure 3c
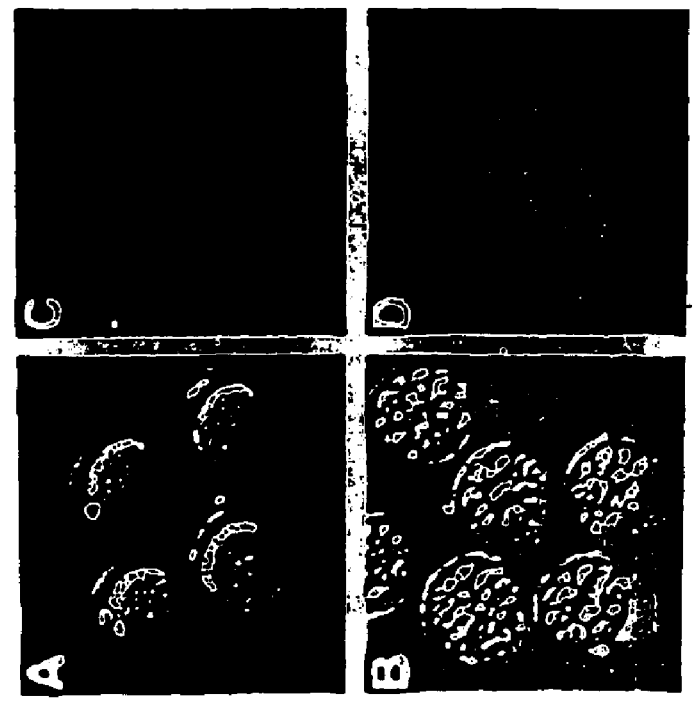
Figure 3e
Figure 3b
Figure 3d

PROTECTION OF THE FEMALE REPRODUCTIVE SYSTEM FROM NATURAL AND ARTIFICIAL INSULTS

FIELD OF THE INVENTION

The present invention relates to methods for protecting female reproductive system against natural or artificial insults by administering a composition comprising an agent that antagonizes one or more acid sphingomyelinase (AS-Mase) gene products. In particular, this invention relates to a method of protecting ovaries from cancer therapy regimens, chemotherapy and radiotherapy, by administering to women a composition containing sphingosine-1-phosphate, or an analog thereof, prior to the therapy. Methods to enhance ovarian functions, ameliorate symptoms of menopause, and improve the success of in vitro fertilization are also disclosed.

I. BACKGROUND OF THE INVENTION

Female gonads house a finite number of meiotically-arrested germ cells (oocytes) enclosed within primordial follicles that serve as the stockpile of eggs released at ovulation at each menstrual cycle for potential fertilization. Gougeon, *Endocr Rev.* 17, 121 (1996); Morita & Tilly, *Dev. Biol.* 213 (1999). Once depleted, the ovarian germ cell pool cannot be replenished. Thus, exposure of women to a wide spectrum of agents that damage the ovary, such as chemotherapeutic agents and radiotherapy, generally leads to premature menopause and irreversible sterility. Waxman, *Soc. Med.* 76, 144 (1983); Familiari et al., *Hum. Reprod.* 8, 2080 (1993); Ried & Jaffe, *Semin. Roentgenol.* 29, 6 (1994); and Reichman & Green, *Monogr. Natl. Cancer Inst.* 16, 125 (1994).

Apoptotic cell death plays a fundamental role in normal germ cell endowment and follicular dynamics in the ovary. Tilly & Ratts, *Contemp. Obstet. Gynecol.* 41, 59 (1996); Tilly, *Rev. Reprod.* 1, 162 (1996); and Tilly et al., *Cell Death Differ.* 4, 180 (1997). Cell fate in the ovary is likely dependent on the actions of several proteins recently identified as key determinants of cell survival or death (Adams & Cory, *Science* 281, 1322 (1998); Green, *Cell* 94, 695 (1998); Thornberry & Lazebnik, *Science* 281, 1312 (1998); Reed, *Oncogene* 17, 3225 (1998); Korsmeyer, *Cancer Res.* 59, 1693 (1999). Among these identified in the ovary are p53 (Tilly et al., *Endocrinology* 136, 1394 (1995); Keren-Tal et al., *Exp. Cell Res.* 218, 283 (1995); and Makrigiannakis et al., *J. Clin. Endocrinol. Metab.* 85, 449 (2000)), members of the bcl-2 gene family (Tilly et al., *Endocrinology* 136–232 (1995); Ratts et al., *Endocrinology* 136, 3665 (1995); Knudson et al., *Science* 270, 99 (1995); Perez et al., *Nature Med.* 3 1228 (1997); Kugu et al., *Cell Death Differ.* 5, 67 (1998); Perez et al., *Nature Genet.* 21, 200 (1999), and members of the caspase gene family (Flaws et al., *Endocrinology* 136, 5042 (1995); Perez et al., *Nature Med.* 3, 1228 (1997); Maravei et al., *Cell Death Differ.* 4, 707 (1997); Kugu et al., *Cell Death Differ.* 5, 67 (1998); Boone & Tsang, *Biol. Reprod.* 58, 1533 (1998); Bergeron et al., *Genes Dev.* 13, 1304 (1998); and Perez et al., *Mol Hum Reprod.* 5, 414 (1999)).

In addition, ceramide, a recently identified lipid second messenger associated with cell death signaling (Spiegel et al., *Curr. Opin. Cell Biol.* 8, 159 (1996); Hannun, *Science* 274, 1855(1996); and Kolesnick & Kronke, *Annu. Rev. Physiol.* 60, 643 (1998)) has been implicated in the induction of apoptosis in the ovary (Witty et al., *Endocrinology* 137, 5269 (1996); Kaipia et al., *Endocrinology* 137, 4864 (1996); and Martimbeau & Tilly, *Clin. Endocrinol.* 46, 241(1997)).

Since the initial discovery of the sphingomyelin pathway, numerous studies have been published on the potential role of ceramide in signaling cell death (Hannun, (1996) id.; and Kolesnick & Kronke (1998) id. It is now known that ceramide can also be metabolized via ceramidase to sphingosine, which is then phosphorylated by sphingosine kinase to generate sphingosine-1-phosphate (S1P) (Cuvillier et al., *Nature* 381, 800 (1996); Spiegel et al., *Ann. N.Y. Acad. Sci* 845, 11 (1998); and Spiegel, *J. Leukoc. Biol.* 65, 341 (1999)).

In some cell types, S1P can effectively counterbalance stress-kinase activation and apoptosis induced by membrane-permeant ceramide analogs or external stressors known to work through elevations in intracellular ceramide levels. Therefore, a rheostat model has been proposed in which cell fate is controlled by shifts in the balance between ceramide and S1P levels. However, the physiologic importance of ceramide, and that of sphingomyelin hydrolysis as a whole, in activating developmental or homoeostatic paradigms of apoptosis have recently been questioned by some investigators (Hofmann & Dixit, *Trends Biochem. Sci* 23, 374 (1998); and Watts et al., *Cell Death Differ.* 6, 105 (1999)). In particular, Hofmann et al., describe a lack of developmental defects that should be the consequence of impaired apoptosis in the acid sphingomyelinase (ASMase) gene knockout mouse as substantive evidence against a role for ASMase-catalyzed sphingomyelin hydrolysis and ceramide in signaling cell death (Kolesnick & Kronke (1998) id.)

Earlier studies using pharmacologic and genetic approaches have shown that several other components of the programmed cell death regulatory pathway in oocytes, including Bcl-2 family members (Ratts et al., *Endocrinology* 136, 3665 (1995); Perez et al., *Nat. Med.* 3, 1228 (1997); Morita et al., *Mol. Endocrinol.* 13, 841 (1999); Perez et al., *Nat. Genet.* 21, 200 (1999)); and caspases (Perez et al., (1997) id.; Bergeron et al., *Genes Dev.* 12, 1304 (1998)), are required for oocyte survival or death. However, cell lineage specificity will certainly be an important issue to consider based on observations that p53, a classic signaling molecule for cancer therapy-induced tumor cell destruction (Ko & Prives, *Genes Dev.* 10, 1054 (1996); and Ding et al., *Crit. Rev. Oncog.* 9, 83 (1998)), is completely dispensable for oocyte death initiated by cancer therapy (Perez et al., (1997) id.)

Although the sensitivity of oocytes to cancer therapy, and the potential role of ceramide in signaling cell death are reported, as evidenced above, little is known regarding the mechanisms responsible for female germ cell destruction. Recently, it has been shown that female mouse oocytes undergo a type of cell death, referred to as apoptosis, when exposed in vitro to a prototypical anti-cancer drug (doxorubicin, 14-hydroxydaunorubicin, Adriamycin®). Perez et al., (1997) id. Moreover, it is shown that culture of mouse oocytes in vitro with sphingosine-1-phosphate protected the oocytes from death induced by subsequent doxorubicin exposure. However, the protection was only tested in vitro with only a single drug, and thus in vivo application remained questionable.

The present invention is the first to show that protection of the ovaries from natural or artificial insults is achieved in vivo, and that this protection is accomplished by administration of a composition containing an agent that antagonizes activity or expression of one or more acid sphingomyelinase (ASMase) gene products. The invention demonstrates that such agents have promising therapeutic effects in combating ovarian failure, thus, preserving fertility and normal ovarian functions under various adverse conditions.

II. SUMMARY OF THE INVENTION

The present invention provides a method of protecting female reproductive system against a natural or an artificial insult comprising: administering a composition comprising an agent that antagonizes one or more acid sphingomyelinase (ASMase) gene product, in an amount sufficient to protect said female reproductive system from normal or pre-mature aging or destruction caused by said natural or artificial insult. The artificial insult comprises chemical insult, radiation insult, surgical insult, or a combination thereof. Natural insults to reproductive system occurs as a consequence of aging, genetic background, physiological factors, environmental factors, or other developmental and genetic factors.

According to an object of the invention, the artificial insult comprises chemical insults, including for example, cytotoxic factors, chemotherapeutic drugs, hormone deprivation, growth factor deprivation, cytokine deprivation, cell receptor antibodies, and the like. Chemotherapeutic drugs include 5FU, vinblastine, actinomycin D, etoposide, cisplatin, methotrexate, doxorubicin, among others.

In accordance with another object of the invention, the artificial insult comprises radiation insult, including ionization radiation, x-ray, infrared radiation, ultrasound radiation, heat, or a combination thereof. Radiation is administered to a patient through an invasive radiation therapy, a non-invasive radiation therapy, or both.

Protection of female's reproductive system is achieved in females in all age groups consisting of pre-reproductive age, reproductive age and post-reproductive age group.

One of the preferred agents of this invention is a small molecule compound comprising lysophospholipid. More preferably the lysophospholipid is a sphingolipid compound, or an analog thereof. The most preferred agent of the invention is the compound of sphingosine-1-phosphate, or an analog thereof. The agent is administered in vitro, ex vivo, or in vivo. Preferred routes of administration include, orally, intravascularly, intraperitoneally, intrauterine, intra-ovarian, subcutaneously, intramuscularly, rectally, topically, or a combination thereof. Intra-ovarian administration is achieved by methods, including, for example, by direct injection into the ovary. The injection is made to the ovary in vivo or ex vivo.

According to another object of the invention, a method of preserving, enhancing, or reviving ovarian function in female mammals is disclosed. This method comprises administering to female mammals an effective amount of a composition comprising sphingosine-1-phosphate, or an analog thereof. The ovarian functions include fertility and normal menstrual cyclicity.

Yet another object of the invention is a method to prevent or ameliorate menopausal syndromes. Menopausal syndromes within the scope of this invention include somatic disorders, cognitive disorders, emotional disorders, and the like. The agent of the invention is administered on a regular daily, weekly, biweekly, monthly or annual intervals in order to achieve the intended therapeutic objective.

According to another object of the invention, an in vitro fertilization method is disclosed that comprises (a) obtaining at least one oocyte from a mammal; (b) incubating said oocyte in a medium containing sphingosine-1-phosphate, or an analog thereof, in an amount sufficient to maintain viability of said oocyte in culture; (c) fertilizing in vitro said oocyte with sperm to produce at least one fertilized oocyte (zygote); (d) culturing said fertilized oocyte to produce an embryo; and (e) transferring at least one embryo to the uterus of said mammal, wherein said at least one embryo develops to term in said mammal.

III. BRIEF DESCRIPTION OF THE FIGURES

FIG. 1. Postnatal oocyte hyperplasia results from ASMase gene disruption. Number of non-atretic primordial, primary and small preantral follicles in young adult (day 42 postpartum) wild-type (hatched bars) and ASMase gene knockout (solid bars) female mice (mean±SEM, n=3 mice per genotype; $P<0.05$ versus respective wild-type value).

FIG. 2. ASMase-deficiency or sphingosine-1-phosphate treatment attenuates programmed cell death in female germline during fetal gametogenesis. (A) Rate of programmed cell death in germline of ovaries obtained from wild-type (+/+) or ASMase-mutant (−/−) female fetuses following in vitro culture without hormonal support. Each data point represents the mean (±SEM) number of non-apoptotic germline remaining per ovarian section, and the results are the combined data from 6 fetal ovaries per genotype ($P<0.05$ versus respective wild-type value). (B) Effects of fumonisin-B1 (FB1) and S1P on germ cell survival in wild-type fetal ovaries cultured for 72 hours without hormonal support (mean±SEM, n=6 fetal ovaries per group). Over one-half of the starting population of germline (0 h or Time 0) is preserved after 72 hours of hormone deprivation by either ASMase gene disruption or by S1P treatment.

FIG. 3. Cell autonomous nature of the germline programmed cell death defect caused by ASMase gene disruption or S IP treatment. Representative analysis of cellular morphology (A, B) and of DNA integrity as assessed by the comet assay (C, D) in pools of non-apoptotic oocytes (ASMase-deficient oocytes treated with doxorubicin or DXR; A, C) and apoptotic oocytes (wild-type oocytes treated with DXR; B, D). (E) Apoptotic cell death response in wild-type (+/+) versus ASMase-deficient (−/−) oocytes cultured without (control, CON) or with 200 nM DXR for 24 hours, or in wild-type oocytes microinjected with human recombinant ASMase or human recombinant Bax. Mean±SEM from 3 or more independent experiments with the total number of oocytes used per group indicated over the respective bar, $P<0.05$ versus respective wild-type value, N.D., none detected. For both ASMase and Bax microinjection, a significant ($P<0.05$) increase in apoptosis was observed versus those levels observed in comparable numbers of vehicle-injected oocytes cultured in parallel (20±5%; mean±SEM, n=3 or more independent experiments).

Figure 4:
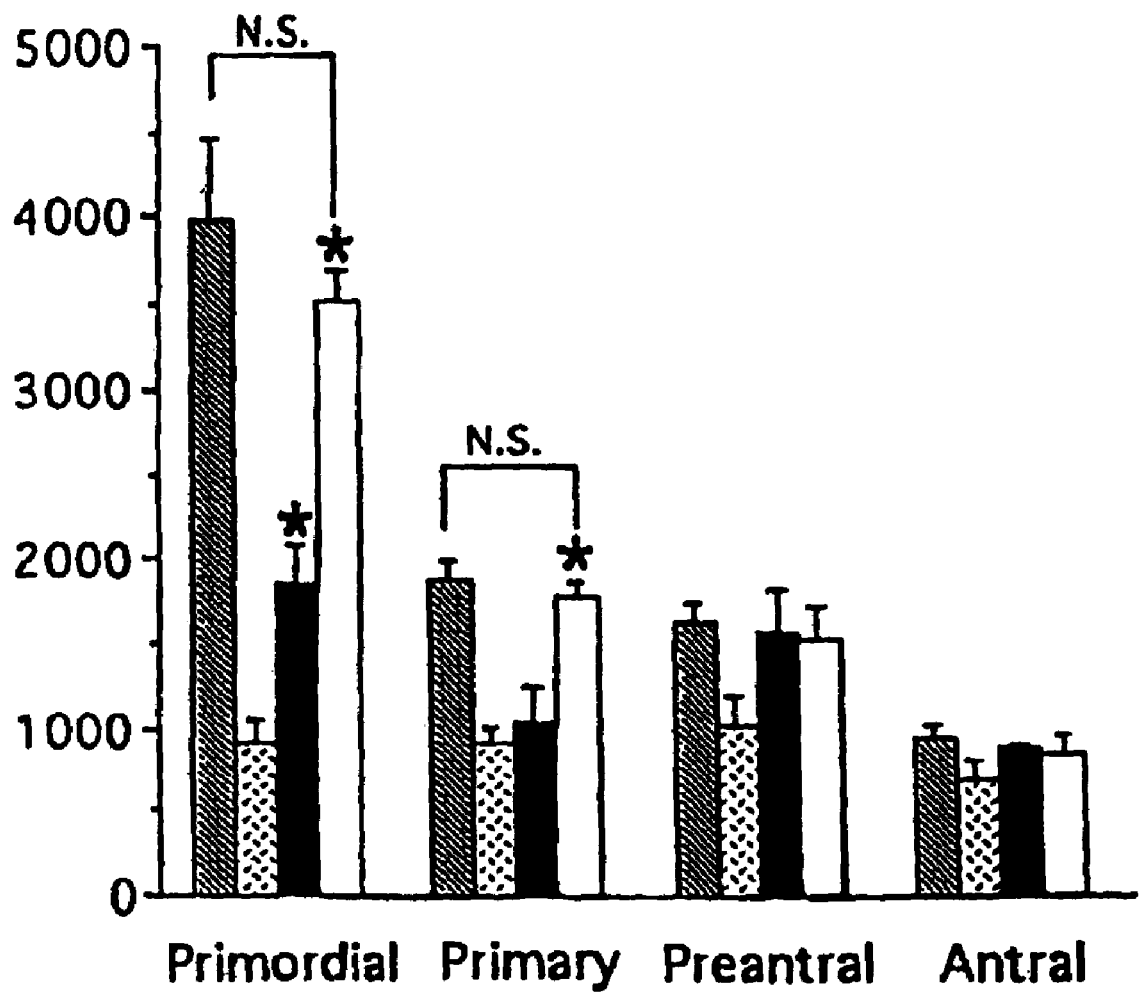

FIG. 4. Complete protection of the female germline from radiation-induced death in vivo by S1P administration. Morphometric analysis of the number of non-atretic oocyte-containing follicles at the four indicated stages of development remaining in vehicle (PET)- or S1P-treated ovaries 14 days after a single treatment with 0.1 Gy of ionizing radiation (mean±SEM, n=3 mice; $P<0.05$ versus 0 μM S1P receiving radiation treatment; N.S., not significantly different).

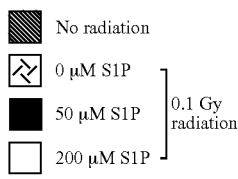

IV. DETAILED DESCRIPTION OF THE INVENTION

This invention, as described herein, relates that compositions containing a novel therapeutic agent, administered in vivo or used in vitro, which protects female reproductive system from stress signals or insults induced by natural or artificial factors.

Apoptosis is a mechanism by which cells are programmed to die under a wide range of physiological, biochemical and developmental stimuli. Apoptosis is also an important cellular response to a large variety of stress signals, induced by natural or artificial factors. Acid sphingomyelinase (ASMase) gene disruption is shown to suppress normal apoptotic deletion of oocytes, leading to ovarian hyperplasia. Ex vivo, ASMase−/− oocytes or wild-type oocytes treated with an agent, capable of antagonizing one or more ASMase gene products, resist developmental and anticancer treatment-induced apoptosis, thereby confirming cell autonomy of the death defect.

The invention, as disclosed and described herein, provides for a germ cell-autonomous death defect caused by ASMase-deficiency. Cell autonomous death is reversed by inhibition of ASMase gene products, which inhibition causes a significant hyperplasia of the female germline during fetal ovarian development. These data, demonstrate that antagonizers of ASMase gene products confer significant protection against natural or artificial insults on oocytes in vivo, or in vitro and, therefore, offer a new route for rapid therapeutic development to combat premature ovarian failure, and to prolong ovarian function and fertility in women.

At present, how antagonizers of ASMase gene products exert their pro- and anti-apoptotic effects in a female reproductive system remains to be elucidated. Without being limited to any specific mechanism of action underlying the invention described herein, one possible mechanism is that a stepwise program of cell death is activated in germline by both physiologic and pathologic stimuli, with alterations in the sphingolipid rheostat serving as an initial signal transduction pathway. Indeed, S1P has been shown to prevent activation of downstream executioner caspases in Jurkat T-cells exposed to short-chain ceramide analogs (Cuvillier et al., *J. Biol. Chem.* 273,2910(1998)), and ceramide has recently been implicated as a facilitator of Bax-induced cytochrome c release from mitochondria (Pastorino et al., *J. Biol. Chem.* 274, 31734 (1999)).

The direct connection between ceramide and Bax is especially relevant to the present invention since Bax-deficient oocytes are, like ASMase-deficient oocytes, resistant to cancer therapy-induced apoptosis (Perez et al., *Nature Med.* (1997) id.) Furthermore, microinjection of human recombinant Bax protein into oocytes duplicates the pro-apoptotic effects of both human recombinant ASMase microinjection and anti-cancer drug treatment (FIG. 3E).

The ASMase antagonizers, or the "agent" according to this invention, include any compound, that suppresses or inhibits activity and/or expression of one or more acid sphingomylinase (ASMase) gene products in vitro, ex vivo, or in vivo. The agent comprises, for example, any lipid, lysophospholipid, sphingolipid, protein, peptide, polypeptide, nucleic acid molecule, including DNA, RNA, DNA/RNA hybrids or an antisense molecule, small molecules, antibiotics, and the like. The terms protein, peptide, and polypeptide are used interchangeably herein.

A preferred agent according to the invention is a small molecule. In a more preferred embodiment of the invention, the agent comprises lysophospholipids, and most preferably, the agent is sphingosine-1-phosphate (S1P), or an analog thereof. Examples of analogs of sphingosine-1-phosphate include but are not limited to, N,N-dimethylsphingosine-1-phosphate; N,N,N-trimethylsphingosine-1-phosphate; N-acetylsphingosine-1-phosphate; N-acylsphingosine-1-phosphate; sphingosine-1,3-diphosphate; sphingosine-3-phosphate; sphingosine-1-thiophosphate; N,N-dimethylsphingosine-1-thiophosphate; N,N,N-trimethylsphingosine-1-thiophosphate; or pharmaceutically acceptable salts thereof.

Sphingosine-1-phosphate is shown to be completely safe and without side effects on the ovaries. In one general embodiment of the invention, as disclosed herein, in vivo administration of the agent of the invention prior to an artificial insult resulted in a significant preservation of the germ cell reserve with complete protection of the quiescent (primordial) and growing (primary, preantral) follicle populations in ovaries exposed to the insult.

According to one general embodiment of the invention, artificial insults are the consequence of a therapy against a disease or a disorder. The disease or disorder comprises, for example, cancer, rheumatoid arthritis, angioplasy, or restenosis. Cancer includes, for example, colon carcinoma, pancreatic cancer, breast cancer, ovarian cancer, fibrosarcoma, myxosarcoma, liposarcoma, chondrosarcoma, osteogenic sarcoma, chondroma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, acute lymphocytic leukemia and acute myelocytic leukemia, chronic leukemia and polycythemia vera, lymphoma (Hodgkin's disease and non-Hodgkin's disease), multiple myeloma, Waldenstrom's macroglobulinemia, or immunoglobulin heavy chain diseases.

Artificial insults, according to the invention described herein, include chemical, radiation, and surgical insults. Examples of chemical insults include, cytotoxic factors, chemotherapeutic drugs, hormone deprivation, growth factor deprivation, cytokine deprivation, cell receptor antibodies and the like. Further non-limiting examples include TNF-alpha, TNF-beta, IL-1, INF-gamma, IL-2, insulin-like growth factor, transforming growth factor B1, vascular endothelial growth factor, fibroblast growth factor, 5FU, vinblastine, actinomycin D, etoposide, cisplatin, methotrexate, doxorubicin, and the like.

In accordance with another embodiment of the invention, the insult is a radiation insult. It is shown that germline of female mammals exposed to radiation are seriously damaged and administration of the composition of the invention in vivo, in vitro, or ex vivo protects oocytes from destruction induced by a therapeutically-relevant dose of ionizing radiation.

Radiation insult, according to the invention disclosed herein, encompasses both non-invasive (external) and invasive (internal) radiation therapies. In an external radiation therapy, treatment is affected by radiation sources outside the body, whereas in an invasive radiation therapy treatment is affected by radiation sources planted inside the body. The representative diseases treated by non-invasive or invasive radiation therapy include, for example, cancer, rheumatoid arthritis, angioplasy, or restenosis.

Invasive radiation therapy encompasses, for example, selective internal radiation therapy (SIRT), incorporation of the radioactive materials into small particles, microspheres, seeds, wires and the like. These objects are directly implanted into the various tissue, organs, or their respective arterial blood supply within the body.

Various methods for introducing radiation into an area treated for stenosis are known. Some methods deliver radiation in a solid medium, while others utilize liquid sources. For example, a procedure in reducing the restenosis rate is the introduction of radiation energy into the interior of the vessel. This procedure, known as "intravascular radiation therapy" (IRT) has been shown to inhibit fibroblast and smooth muscle cell hyperplasia.

U.S. Pat. No. 5,059,166, issued to Fischell, discloses an IRT method that relies on a radioactive stent that is permanently implanted in the blood vessel after completion of the lumen opening procedure. U.S. Pat. No. 5,302,168, issued to Hess, teaches use of a radioactive source contained in a flexible catheter. U.S. Pat. No. 5,503,613, issued to Weinberger, uses a liquid filled balloon to guide a solid source wire to a treatment site. U.S. Pat. No. 5,616,114, issued to Thornton et al., describes an apparatus and method for delivering liquid radiation into a balloon-tipped catheter. Radiation therapies disclosed by aforementioned patents, are disclosed merely as examples of radiotherapeutic regimens used to treat patients and are non-limiting.

The use of radioactive material in connection with therapies, such as those disclosed above, creates a risk of harmful exposure, both to the medical personnel and to patients. Precautionary measures need to be taken to protect against the harm caused by the leakage of liquid radiation into the blood stream during these therapies. Sensitive organs, such as the ovaries, are inevitably damaged depending on the invasiveness of the procedure used. The invention disclosed herein protects ovaries of both patients and medical personnel from a risk of harm caused by exposure to radiation during such therapies.

Radiation is emitted from a variety of radionuclides. These radionuclides encompass, for example, beta-ray emitters, gamma-ray emitters, or a radionuclide that emits both beta-ray and gamma-ray. Further examples of radionuclides include, Strontium 90, Iridium 192, Phosphorous 32, Rhenium 186, Rhenium 188, $^{198}$Au, $^{169}$Er, $^{166}$Ho, $^{153}$Sm, and $^{165}$Dy, which are chosen according to the purpose of treatment.

Other radiation sources include sources used in nuclear magnetic resonance diagnosis in which the central ion of the complex salt must be paramagnetic. In particular, the radiation sources use the divalent and trivalent ions of the elements of atomic numbers 21–29, 42, 44 and 58–70. Suitable ions are, for example, the chromium(III), manganese(II), iron(II), nickel(II), copper(II), praseodymium(III), neodymium(III), samarium(III), ytterbium(III), gadolinium (III), terbium(III), dysprosium(III), holmium(III), erbium (III), and iron(III).

According to another embodiment of the invention disclosed herein, radiation insult includes ultrasound radiation. Ultrasound radiation is administered to patients, either alone or in combination with other therapies, for example, hormonal therapy, chemotherapy, or surgery. The therapeutic regimen is applied either preoperatively, i.e., to the tumor in situ or postoperatively, in the region of the tumor after removal of the primary cancerous lesion. The ultrasound therapy comprises both the invasive and non-invasive ultrasound treatments. The dosage of ultrasonic energy applied is, for example, above 22.5 watt/sec, and has a frequency in the range of, for example, about 1 KHz to about 3 MHz.

According to another embodiment of this invention, radiation insult includes, x-ray, infrared, and heat. Heat is used to selectively induce apoptosis in intended cells or tissues. Preferably heat is used to treat inflammation. The term inflammation includes inflamed atherosclerotic plaques, restenosis, and arteritis such as that found in systemic lupus, myocarditis of the autoimmune etiology, arteriovenous fistulea, dialysis grafts or other vascular prosthesis. The phrase "treating inflammation" also includes treating a region of a vein prior to or after balloon angioplasty, or related interventions that could result in inflammation and subsequent thrombosis, acute closure or restenosis.

Heat may be transferred to the target cells by a variety of methods. For example, heat is transferred into an inflamed plaque in a blood vessel by means of a catheter, stent, or liquid heat. Catherter or stents are heated electrically or with microwave or radio frequency radiation or other means. Heat is also generated from internal or external devices, such as radio frequency sources outside the body. The present invention protects ovaries from the risk of over-exposure to heat waves or liquid heat during heat therapy.

Natural insults, as defined herein, include damages resulting from physiological, biochemical or developmental processes occurring in a female body. A manifest natural, insult is apoptosis due to aging. Natural insults are influenced, for example, by genetic background of the female, environmental affects, or both. The functional life span of female gonads is defined by the size and rate of depletion of the endowment of oocytes enclosed within follicles in the ovaries at birth. This continuous loss of oocytes throughout life, referred to by many as the female biological clock, is driven by a genetic program of cell death that is controlled by physiological and biochemical pathways and players and is conserved from worms to humans (Morita & Tilly (1999) id.) This invention, as disclosed herein, demonstrates the effect of antagonizers of ASMase gene products in combating normal or pre-mature germ cell depletion in a female mammal.

Without being limited to any specific mechanism of action underlying the invention described herein, one possible mechanism for the effect of antagonizers of ASMAse gene products is through preventing apoptosis of granulosa cells as well as, or instead of, directly preventing apoptosis of oocytes. Granulosa cells support, nourish, and help to mature oocytes throughout postnatal life.

Examples of disease and disorders resulting from a natural insult include, disturbances in menstruation, abnormal uterine bleeding, abnormal ovulatory cycles, amenorrhea, pelvic pain, sexual dysfunction, in fertility, menstrual cyclicity, and pre-mature menopause among others.

Other insults include surgical insults wherein a woman's reproductive system, in part or in whole, is surgically removed. In particular, hormonal imbalance, resulting from the removal of one or both ovaries, is fully or partially restored by administration of the therapeutic agent of the invention.

Reproductive system includes any cell, tissue, organ, and tract that are involved in part or in whole in sexual reproduction. Cells include variety of somatic cells, for example, granulosa cells that nourish and mature oocytes, as well as germ cells.

Included withing the scope of this invention are methods to protect women's ovaries from natural and artificial insults, not only to keep them fertile, but also to preserve enough ovarian function to prevent menopause and its associated disorders. Women are subject to natural or artificial insult in any age group. These age groups are pre-reproductive, reproductive or post-reproductive age groups. Pre-mature menopausal syndromes are initiated by a wide variety of artificial or natural conditions. Menopausal disorders, include, for example, somatic disorders such as osteoporosis, cardiovascular disease, somatic sexual dysfunction, loss of libido; cognitive disorders, such as loss of memory; emotional disorders, such as depression, and the like.

The composition of the invention is administered on a continuous or semi-continuous, or temporary basis, depending on the type of insult and objectives of the therapy intended. For example, if protection of the reproductive system from long term natural insults is intended, administration of the composition of this invention on a continuous or semi-continuous basis is preferred. In a continuous administration, the composition is generally administered regularly, on a predetermined interval, for an indefinite period of time. Predetermined intervals comprise daily, weekly, biweekly, or monthly, or yearly intervals.

If protection from artificial insults are intended both short term and long term administration are suggested, depending on the type of insult and the objective of the therapy intended. An example of a short term administration is the administration to protect ovaries from radiation or chemical insults. In short term administration, the composition is administered, at least once, in a period of from about thirty days prior to immediately prior to exposure to the insult. More preferably the composition is administered from about fifteen days to about two days, and most preferably from about seven days to about two hours prior to exposure to the insult. The administration of the composition is terminated prior to ovarian exposure to the insult, or it is continued during exposure or after the exposure is terminated.

The dosage of the therapeutic agent is adjusted according to, for example, the duration and the objective of the treatment intended. A lower dosage of the agent is required in a more prolonged and continuos administration.

The administration is achieved in vivo, in vitro or ex vivo. The in vivo administration encompasses orally, intravascularly, intraperitoneally, intra-uterine, intra-ovarian, subcutaneously, intramuscularly, rectally, topically, or a combination thereof. Intra-ovarian administration is achieved by several methods, including, for example, by direct injection into the ovary. The injection is made to the ovary in vivo or ex vivo.

According to another aspect of this invention, an in vitro fertilization method is described that uses the therapeutic agent of this invention to protect the viability of female germline at different stages of in vitro fertilization. These stages, include in vivo, ex vivo, and in vitro periods of fertilization and pregnancy. In vivo stages of fertilization and pregnancy include, for example, one or more of the following periods: the period prior to isolation of oocytes, the period after implantation of the embryo in the uterus, and the period during pregnancy. In vitro, and ex vivo stages include, for example, one or more of the following: cryopreservation of oocytes, culture or growth of oocytes prior to fertilization, fertilization stage, culture or growth of embryo post-fertilization.

Oocytes isolated from women are at different stages of development and are either mature or immature. Immature oocytes reach maturity in vitro or in vivo conditions. In vitro fertilization, according to the invention, is achieved by the use of a mammal's own oocytes or a different mammal's oocytes. After the embryo is implanted in the subject mammal, in vivo administration of the therapeutic agent is terminated, or it is continued for a time period thereafter to ensure continued viability and normal development of the embryo in vivo.

In vitro fertilization method, according to the invention disclosed and described herein, increases the chances of successful fertilization, pregnancy and normal development of the embryo in the uterus. Furthermore, it ensures availability of immature or mature oocytes for fertilization, and makes it possible to preserve fertility and increases availability of donor oocytes for women who do not have their own functional oocytes.

Also embraced within the scope of this invention are compositions comprising one or more agents of the invention in association with one or more non-toxic, pharmaceutically acceptable carriers and/or diluents and/or adjuvants (collectively referred to herein as "carrier" materials) and, if desired, other active ingredients.

According to an embodiment of the invention, the agent is combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Formulations for parenteral administration are, for example, in the form of aqueous or non-aqueous isotonic sterile injection solutions or suspensions. These solutions and suspensions are prepared, for example, from sterile powders or granules having one or more of the carriers or diluents mentioned for use in the formulations for oral administration. The compounds may be dissolved in water, polyethylene glycol, propylene glycol, ethanol, corn oil, cotton seed oil, peanut oil, sesame oil, benzyl alcohol, sodium chloride, and/or various buffers. Other adjuvants and modes of administration are well and widely known in the pharmaceutical art.

The compositions of the invention are adapted to be administered by any suitable route, and in a dose effective for the treatment intended. Therapeutically effective doses of the composition required to prevent or preserve the female reproductive system from insults are readily ascertained by one of ordinary skill in the art.

For oral administration, the composition is in the form of, for example, a tablet, capsule, suspension or liquid. The composition is preferably made in the form of a dosage unit containing a particular amount of the active ingredient. Examples of such dosage units are tablets or capsules. Preferably, the oral units contain an amount of active ingredient from about 1 to 1000 mg, more preferably from about 25 to 500 mg, and most preferably from about 100 to 250 mg. A suitable daily dose may vary widely, however, a dose of from about 0.01 to 3000 mg/kg body weight, or from about 0.1 mg to about 100 mg/kg of body weight per day is preferred. A more preferred dosage will be a range from about 1 mg to about 100 mg/kg of body weight. Most preferred dosage is a dosage in a range from about 1 to about 50 mg/kg of body weight per day.

The dosage regimen of the agents and/or compositions of this invention is selected in accordance with a variety of factors and thus may vary widely. A main factor to consider is the objective of therapy, for example, protecting female germline from radiation or chemotherapy, prolonging fertility, preventing menopause, preserving normal menstrual cyclicity, ameliorating or preventing post-menopausal conditions, are among many therapeutic objectives that are intended and encompassed within the scope of the invention. Other factors include, for example, the age, weight, severity and type of the insult, the route of administration, and the type of therapeutic agent employed.

The invention will be more fully understood by reference to the following examples. These examples are not to be construed in any way as limiting the scope of this invention. All literature cited herein is specifically incorporated by reference.

V. EXAMPLES

Example 1

Histomorphometric Evaluation of Oocyte Endowment

Ovaries are fixed (0.34 N glacial acetic acid, 10% formalin, 28% ethanol), embedded in paraffin, and serially sectioned (8 μM). The serial sections from each ovary are aligned in order on glass microscope slides, stained with hematoxylin/picric methyl blue, and analyzed for the number of healthy (non-atretic) oocyte-containing primordial, primary and small preantral follicles as described by Perez et al. *Nat. Genet.* (1999) id. incorporated by reference herein in its entirety.

Example 2

Histomorphometic Evaluation of Wild Type and ASMase–/– Ovaries

ASMase–/– mice are generated as described by Horinouchi et al., *Nat. Genet.* 10, 288 (1995), incorporated herein by reference in its entirety. The histomorphometric evaluation of the oocyte endowment of wild type mice and ASMase–/– sisters shows that sphingomyelin hydrolysis is a key event in generating death signals in the developing female germline. Compared with their wild-type sisters, ASMase–/– females possess over $1.1 \times 10^3$ more quiescent oocyte-containing primordial follicles per ovary, as well as significant hyperplasia of the growing (primary and small preantral) follicle populations. Results are presented in Table 1 and FIG. 1.

TABLE 1

Postnatal Oocyte Hyperplasia Results From ASMase Gene Disruption

| Follicles | +/+ | –/– | P value |
|---|---|---|---|
| Primordial | 19120 ± 602 | 30480 ± 2397 | P < 0.01 |
| Primary | 707 ± 93 | 1573 ± 141 | P < 0.01 |
| Preantral | 13 ± 13 | 160 ± 46 | P < 0.05 |

Number of non-atretic oocyte-containing primordial follicles endowed in the ovarian reserve, and numbers of growing (primary and small preantral) follicles, in wild-type (+/+) and ASMase-mutant (–/–) female mice at day 4 postpartum (mean±SEM, n=3 mice per genotype).

The ovarian oocyte reserve remains significantly elevated in ASMase–/– female mice in young adult life (FIG. 1), well prior to the onset of any organ abnormalities or Niemann-Pick disease-like symptoms that occurs in ASMase–/– mice during postnatal life.

Figure 2B:
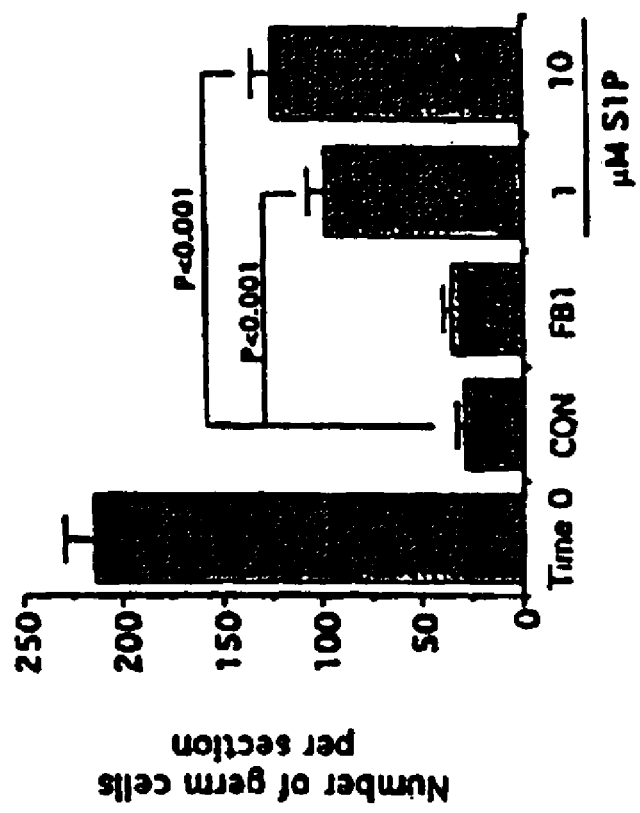
Figure 2A:
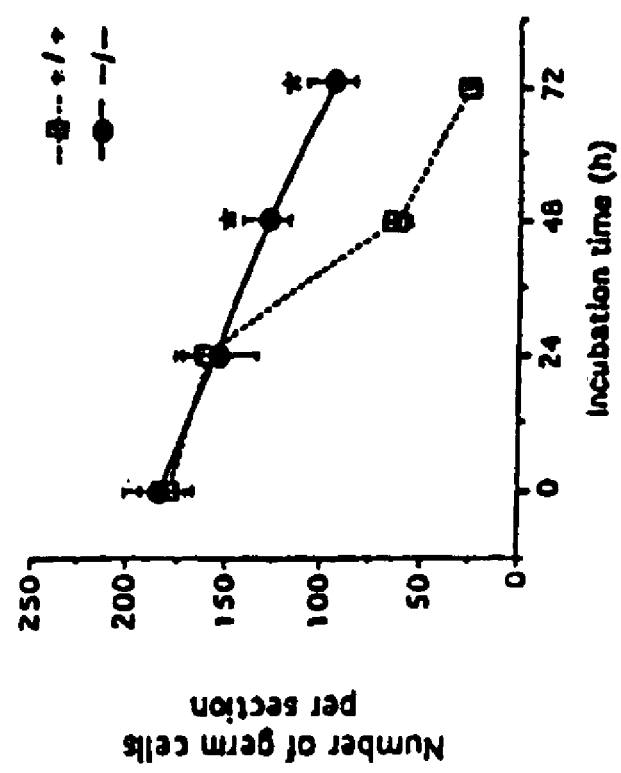

To determine the basis of the extensive oocyte hyperplasia in ASMase–/– neonates, fetal ovaries are harvested from wild-type and mutant mice at embryonic day 13.5 (e13.5) for in vitro culture as a model to recapitulate the events surrounding germline death that occurs as a normal component of female gametogenesis. A time-dependent activation of programmed cell death is observed in germline of wild-type fetal ovaries cultured without hormonal support for up to 72 hours (FIG. 2A). By comparison, the rate of germ cell apoptosis is significantly attenuated in ASMase-deficient fetal ovaries cultured in parallel (FIG. 2A). These findings indicate that there exists an ovarian-intrinsic cell death defect in the ASMase-deficient mouse, and point to enhanced survival of the developing germline during oogenesis as the mechanism underlying the enlarged oocyte pool seen in mutant females at birth.

Example 3

Treatment with Ceramide Synthase Inhibitor

In order to show that sphingomyelin hydrolysis, as opposed to ceramide synthesis, is important for generating ceramide as a death signal, wild-type fetal ovaries are maintained in vitro for 72 hours and various concentrations (5–500 μM) of a ceramide synthase inhibitor, fumonisin-B1 (FB1) are applied to these ovaries. The results show that this treatment does not alter survival rates in female germline (FIG. 2B). Importantly, however, and in support of the rheostat model, the reduced incidence of germ cell apoptosis conveyed by ASMase-deficiency is recapitulated by culturing wild-type fetal ovaries with increasing concentrations of S1P (FIG. 2B). Equivalent levels of in vitro germ cell survival are obtained by either ASMase gene knockout (FIG. 2A) or by S1P treatment (FIG. 2B).

Example 4

Cell Autonomous Nature of Response

To demonstrate that germline survival is a cell autonomous or a germline-intrinsic response, individual oocytes are isolated from adult wild-type and ASMase–/– female mice, and are cultured ex vivo with or without the anti-cancer drug, doxorubicin (DXR), to induce apoptosis. In addition to assessments of cellular morphology and caspase activation, some oocytes in each group are processed for DNA cleavage analysis as an endpoint for cell death using the Trevigen Comet Assay kit. The apoptotic event is elicited in wild-type, but not ASMase-deficient, oocytes by DXR (FIG. 3E).

Example 5

Microinjection Experiment

Human recombinant acid sphingomyelinase is synthesized and purified as described by He et al., *Biochim. Biophys. Acta* 1432, 251 (1999), incorporated herein by reference in its entirety. Six picoliters of vehicle or of a 1 mg/ml stock of the enzyme are microinjected into single oocytes using a Zeiss Axiovert 135 inverted microscope equipped with Narishige micromanipulators and a PLI-100 pico-injector. Oocytes that survived the microinjection procedure (>75%) are then cultured and assessed for the occurrence of apoptosis. Furthermore, microinjection of human recombinant Bax protein into single oocytes and assessments of apoptosis are made as described by Perez, et al. (1997) id. Microinjection of human recombinant Bax protein into oocytes duplicates the pro-apoptotic effects of both human recombinant ASMase microinjection and anti-cancer drug treatment (FIG. 3E). For both ASMase and Bax microinjection, a significant ($P<0.05$) increase in apoptosis is observed versus those levels observed in comparable numbers of vehicle-injected oocytes cultured in parallel (20±5%; mean±SEM, n=3 or more independent experiments).

Example 6

In Vitro Oocyte Cultures

Female mice (43 days of age post-partum; Charles River Laboratories, Wilmington, Mass.) are superovulated with 10 IU of equine chorionic gonadotropin (eCG or PMSG) followed by 10 IU of human chorionic gonadotropin 48 h later. Mature oocytes are collected from the oviducts 16 h after hCG injection. Cumulus enclosed oocytes are denuded by a 1-min incubation in 80 IU/ml of hyaluronidase, followed by three washes with culture medium. The medium used for all culture experiments is human tubal fluid (Irvine Scientific, Santa Ana, Calif.) supplemented with 0.5% bovine serum albumin (BSA).

Oocytes are cultured in 0.1 ml drops of culture medium (8–10 oocytes/drop) under paraffin oil, an incubated with or without DXR (200 nM) and/or fumonisin-B1, sphingosine-1-phosphate or benzyloxycarbonyl-Val-Ala-Asp-fluoromethylketone (zVAD-FMK) for 24 h at 37 C in a humidified atmosphere of 5% $CO_2$-95% air. At the end of the incubation period, oocytes are fixed, stained with Hoechst 33342 and checked microscopically for morphological changes characteristic of apoptosis (condensation, budding, cellular fragmentation, and chromatin segregation into apoptotic bodies). The percentage of oocytes that goes through apoptosis out of the total number of oocytes cultured per drop in each experiment is then determined, and all experiments are independently repeated four to ten times with different mice.

Example 7

In Vitro Embryo Cultures

Female mice are superovulated with eCG followed hCG treatment (see above) and placed with fertile males immediately after hCG injection. Sixteen hours after mating, one-cell embryos (confirmed by the presence of two polar bodies) are harvested from the ampullae and denuded of cumulus cells by a 1-min hyaluronidase treatment. Embryos are then maintained in vitro in HTF supplemented with 0.5% BSA in absence or presence of 200 nM DXR. Under in vitro conditions, one-cell embryos progress to the morula stage of development within 72 h (see in vitro oocyte cultures above for details of methodology and culture conditions). See, Perez et al.(1997) id., incorporated by reference herein in its entirety.

Example 8

Bax-Null Mice

In vitro experiments: mature oocytes are harvested from wild-type and Bax-null adult female mice at approximately 6 weeks of age using the gonadotropin superovulation regimen described above. Following hyaluronidase removal of cumulus cells, oocytes are incubated for 24 h without or with 200 nM DXR, after which the occurrence of apoptosis is assessed and described under in vitro oocyte cultures.

In vivo experiments: age-matched adult wild-type and Bax-null female mice are given two intraperitoneal injections of DXR (10 mg/kg of body weight) 1 week apart, starting at approximately 8 weeks of age post partum. One week following the second injection, ovaries are collected, fixed, embedded in paraffin, serial-sectioned, and stained with hematoxylin/picric methyl blue. Follicular morphology and numbers of immature (primordial) follicles present in each ovary are then assessed as detailed previously.

Example 9 p53-Null Mice

Mature oocytes are collected from adult wild-type and p53 null female mice by superovulation, and incubated with or without 200 nM DXR for 24 h. Following culture, the occurrence of apoptosis is assessed as described above (see, Example 6: in vitro oocyte cultures).

Example 10

S1P Protection Against Radiation

Young adult (postpartum day 40) wild-type female mice are anesthetized, and dorsal incisions are made to retrieve and expose the ovaries. Five μl of vehicle (PET) are injected into the bursa of one ovary of the pair while 5 μl of a stock of either 0.5 or 2 mM S1P, prepared in PET, are injected into the bursa of the contralateral ovary. Based on an estimated bursai cavity volume of 50 μl, the final concentrations of S1P in the bursal cavity for ovarian exposure following administration of the 0.5 and 2 mM stocks are approximately 50 and 200 μM, respectively. The ovaries are returned to the peritoneal cavity, the incisions are sutured, and the mice are allowed to recover for a 2 hour pretreatment period prior to a single exposure to 0.1 Gy of abdominally-directed ionizing radiation. After two weeks, ovaries are collected, coded, and processed for histomorphometric evaluation of non-atretic oocyte-containing follicle numbers as described above (see Example 1). In the absence of irradiation, the number of follicles at any stage of development in S1P-treated ovaries does not significantly differ from the number of corresponding follicles in vehicle-treated ovaries.

Nearly complete destruction (LD$_{80}$) of the oocyte-containing primordial follicle pool is observed in vehicle-treated ovaries of mice two weeks after a single exposure to 0.1 Gy of ionizing radiation (FIG. 4). In contrast, in vivo administration of S1P two hours prior to irradiation resulted in a significant and dose-dependent preservation of the germ cell reserve, with complete protection of the quiescent (primordial) and growing (primary, preantral) follicle populations in ovaries exposed to the highest dose of S1P prior to irradiation (FIG. 4).

Moreover, since oocyte viability, growth and function are required for continued development of follicles from a quiescent to mature state (see, Morita & Tilly (1999) id., incorporated herein by reference in its entirety), the observation that ovaries pretreated with the highest dose of S1P prior to irradiation retained a completely normal distribution of oocyte-containing follicles at all stages of development (i.e., identical to the non-irradiated controls) at two weeks post-irradiation (FIG. 4) suggests that the protected oocytes are indeed viable and functional.

REFERENCES

1. Hannun, *Science,* 274:1855 (1996).
2. Cuvillier et al., *Nature,* 381:800 (1996).
3. Hofmann & Dixit, *Trends Biochem. Sci.,* 23:374 (1998).
4. Watts et al., *Cell Death Differ.,* 6:105 (1999).
5. Horinouchi et al., *Nat. Genet.,* 10:288 (1995).
6. Perez et al., *Nat. Med.,* 3:1228 (1997).
7. Bergeron et al., *Genes Dev.,* 12:1304 (1998).
8. Morita et al., *Mol. Endocrinol.,* 13:841 (1999).
9. Reynolds, J. *Nat. Cancer Inst.,* 91:664 (1999).
10. Morita & Tilly, *Dev. Biol.,* 213:1–17 (1999).
11. Perez et al., *Nat. Genet.,* 21:200 (1999).
12. Morita et al., *Endocrinology,* 140:941 (1999).
13. Bose et al., *Cell,* 82:405 (1995).
14. Merrill et al., *Toxicol. Appl. Pharmacol.,* 142:208 (1997).
15. Perez et al., *Mol. Hum. Reprod.,* 5:414 (1999).
16. Van Brocklyn et al., *J. Cell Biol.,* 142:229 (1998).
17. Van Brocklyn et al., *J. Biol. Chem.,* 274: 4626 (1999).
18. Edsall et al., *J. Neurosci.,* 17:6952 (1997).
19. Goetzl & An, *FASEB J,* 12:1589 (1998).
20. Hla et al., *Biochem. Pharmacol.,* 58:201 (1999).
21. Gosden, *Nature,* 383:485 (1996).
22. Dong et al., *Nature,* 383:531 (1996).
23. Tilly & Robles in: *Molecular Biology in Reproductive Medicine,* Fauser et al., (Parthenon, New York, 1999), Chapter 5, pp. 79–101.
24. Briggs et al., in: *Molecular Biology in Reproductive Medicine,* Fauser et al., (Parthenon, New York, 1999) Chapter 12, pp. 251–269.
25. Ko & Prives, *Genes Dev.,* 10: 1054 (1996).
26. Ding & Fisher, *Crit. Rev. Oncog.,* 9:83 (1998).
27. Cuvillier, *J. Biol. Chem.,* 273:2910 (1998).
28. Pastorino et al., *J. Biol. Chem.,* 274:31734 (1999).
29. He et al., *Biochim. Biophys. Acta.,* 1432:251 (1999).
30. Jürgensmeier et al., *Proc. Natl. Acad. Sci. USA,* 95:4997 (1998).
31. Tilly & Johnson in: *Apoptosis and Cancer Chemotherapy,* Hickman & Dive, (Humana Press, Totowa, N.J.), Chapter 17, pp. 257–273.
32. Kolesnick & Krönke, *Annu. Rev. Physiol.,* 60:643 (1998).
33. S. Spiegel, *J. Leukoc. Biol.,* 65:341 (1999).
34. S. Spiegel et al., *Ann. N.Y. Acad. Sci.,* 845:11 (1998).
35. Adams & Cory, *Science* 281, 1322 (1998).
36. Green, *Cell* 94, 695 (1998).
37. Thornberry & Lazebnik, *Science* 281, 1312 (1998).
38. Reed, *Oncogene* 17, 3225 (1998).
39. Korsmeyer, *Cancer Res.* 59, 1693 (1999).
40. Tilly et al., *Endocrinology* 136, 1394 (1995).
41. Keren-Tal et al., *Exp. Cell Res.* 218, 283 (1995).
42. Makrigiannakis et al., *J. Clin. Endocrinol. Metab.* 85, 449 (2000)).
43. Tilly et al., *Endocrinology* 136–232 (1995).
44. Ratts et al., *Endocrinology* 136, 3665 (1995).
45. Knudson et al., *Science* 270, 99 (1995).
46. Kugu et al., *Cell Death Differ.* 5, 67 (1998).
47. Flaws et al., *Endocrinology* 136, 5042 (1995).
48. Maravei et al., *Cell Death Differ.* 4, 707 (1997).
49. Boone & Tsang, *Biol. Reprod.* 58, 1533 (1998).
50. Martimbeau & Tilly, *Clin. Endocrinol.* 46, 241(1997)).

What is claimed is:

1. A method of treating a female reproductive system by administering to a female patient a composition comprising sphingosine-1-phosphate in an amount sufficient to inhibit apoptosis induced by an artificial insult, wherein said administration is in vivo or ex vivo, and wherein said artificial insult is a chemotherapeutic drug or radiation.

2. The method of claim 1, wherein said chemotherapeutic drug is 5FU, vinblastine, actinomycin D, etoposide, cisplatin, methotrexate, doxorubicin, or a combination thereof.

3. The method of claim 1, wherein said radiation insult is ionization radiation, x-ray, infrared radiation, ultrasound radiation, heat, or a combination thereof.

4. The method of claim 1, wherein said radiation insult comprises an invasive radiation therapy, a non-invasive radiation therapy, or both.

5. The method of claim 1, wherein said female reproductive system comprises ovaries.

6. The method of claim 1, wherein said female reproductive system comprises oocytes.

7. The method of claim 1, wherein said female patient is in a reproductive age.

8. The method of claim 1, wherein said female patient is in a pre-reproductive age.

9. The method of claim 1, wherein said female patient is in a post-reproductive age.

10. The method of claim 1, wherein said composition is administered at least once from about fifteen days to about two days prior to exposure to said insult.

11. The method of claim 10, wherein said composition is administered at about seven days to about two hours prior to exposure to said insult.

12. The method of claim 1, wherein said composition is administered orally, intravascularly, intraperitoneally, subcutaneously, intramuscularly, intra-uterine, intra-ovarian, rectally, topically, or a combination thereof.

13. The method of claim 1, wherein said artificial insult is a result of a therapy against a disease or a disorder.

14. The method of claim 13, wherein said disease or disorder comprises, cancer, rheumatoid arthritis, angioplasty, or restenosis.

15. The method of claim 14, wherein said cancer comprises; colon carcinoma, pancreatic cancer, breast cancer, ovarian cancer, fibrosarcoma, myxosarcoma, liposarcoma, chondrosarcoma, osteogenic sarcoma, chondroma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, acute lymphocytic leukemia and acute myelocytic leukemia, chronic leukemia and polycythemia vera, lymphoma (Hodgkin's disease and non-Hodgkin's disease), multiple myeloma, Waldenstrom's macroglobulinemia, heavy chain diseases, or a combination thereof.

16. The method of claim 1, wherein said female patient is a woman.

17. The method of claim 1, wherein the artificial insult is a chemotherapeutic drug.

* * * * *